US010542902B2

(12) United States Patent
Perschbacher et al.

(10) Patent No.: US 10,542,902 B2
(45) Date of Patent: *Jan. 28, 2020

(54) ATRIAL FIBRILLATION DETECTION

(71) Applicant: Cardiac Pacemakers, Inc., St. Paul, MN (US)

(72) Inventors: David L. Perschbacher, Coon Rapids, MN (US); Deepa Mahajan, North Oaks, MN (US); Howard D. Simms, Jr., Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/967,326

(22) Filed: Apr. 30, 2018

(65) Prior Publication Data
US 2018/0242869 A1 Aug. 30, 2018

Related U.S. Application Data

(63) Continuation of application No. 15/082,440, filed on Mar. 28, 2016, now Pat. No. 9,999,368.
(Continued)

(51) Int. Cl.
A61B 5/046 (2006.01)
A61N 1/39 (2006.01)
(Continued)

(52) U.S. Cl.
CPC .............. *A61B 5/046* (2013.01); *A61B 5/0031* (2013.01); *A61B 5/0245* (2013.01); *A61B 5/042* (2013.01);
(Continued)

(58) Field of Classification Search
CPC ....... A61B 5/0031; A61B 5/046; A61B 5/042; A61B 5/3621; A61B 5/3956;
(Continued)

(56) References Cited

U.S. PATENT DOCUMENTS 5,622,178 A 4/1997 Gilham
6,490,479 B2 12/2002 Bock
(Continued)

FOREIGN PATENT DOCUMENTS

AU 2015301633 B2 8/2018
CN 1829554 A 9/2006
(Continued)

OTHER PUBLICATIONS

"U.S. Appl. No. 14/825,669, Response filed Apr. 24, 2017 to Final Office Action dated Mar. 9, 2017", 12 pgs.
(Continued)

*Primary Examiner* — Paula J Stice
(74) *Attorney, Agent, or Firm* — Schwegman Lundberg & Woessner, P.A.

(57) ABSTRACT

An apparatus includes a sensing circuit configured to generate a sensed physiological signal representative of cardiac activity of a subject, and an arrhythmia detection circuit. The arrhythmia detection circuit is configured to monitor information corresponding to ventricular depolarization (V-V) intervals using the sensed physiological signal; determine a V-V interval distribution; determine a heart rate density index (HRDI) as a portion of samples of the V-V interval distribution corresponding to a V-V interval occurring most often in the distribution; and generate an indication of atrial fibrillation (AF) using the HRDI.

20 Claims, 11 Drawing Sheets

Related U.S. Application Data

(60) Provisional application No. 62/142,184, filed on Apr. 2, 2015.

(51) Int. Cl.
| | |
|---|---|
| *A61B 5/0464* | (2006.01) |
| *A61N 1/362* | (2006.01) |
| *A61B 5/00* | (2006.01) |
| *A61B 5/0245* | (2006.01) |
| *A61B 5/042* | (2006.01) |
| *A61B 5/0432* | (2006.01) |

(52) U.S. Cl.
CPC .......... *A61B 5/0432* (2013.01); *A61B 5/0464* (2013.01); *A61B 5/686* (2013.01); *A61N 1/3621* (2013.01); *A61N 1/3956* (2013.01); *A61N 1/3962* (2013.01); *A61N 1/3987* (2013.01)

(58) Field of Classification Search
CPC ..... A61B 5/0432; A61B 5/0464; A61B 5/686; A61B 5/3962; A61B 5/3987
See application file for complete search history.

(56) References Cited

U.S. PATENT DOCUMENTS

| | | | |
|---|---|---|---|
| 6,931,273 | B2 | 8/2005 | Groenewegen et al. |
| 7,031,765 | B2 | 4/2006 | Ritscher et al. |
| 7,353,057 | B2 | 4/2008 | Schiessle et al. |
| 7,412,282 | B2 | 8/2008 | Houben |
| 7,596,405 | B2 | 9/2009 | Kurzweil et al. |
| 7,657,307 | B2 | 2/2010 | Van Dam et al. |
| 7,899,531 | B1 | 3/2011 | Benser et al. |
| 7,904,142 | B2 | 3/2011 | Kim et al. |
| 8,195,280 | B2 | 6/2012 | Van Dam et al. |
| 8,560,058 | B2 | 10/2013 | Babaeizadeh et al. |
| 8,639,316 | B2 | 1/2014 | Sarkar |
| 9,999,368 | B2 | 6/2018 | Perschbacher et al. |
| 2001/0034539 | A1 | 10/2001 | Stadler et al. |
| 2002/0065473 | A1 | 5/2002 | Wang et al. |
| 2004/0092836 | A1 | 5/2004 | Ritscher et al. |
| 2005/0080347 | A1 | 4/2005 | Sheth et al. |
| 2006/0247548 | A1 | 11/2006 | Sarkar et al. |
| 2007/0100248 | A1 | 5/2007 | Van Dam et al. |
| 2008/0161703 | A1 | 7/2008 | Houben et al. |
| 2009/0112110 | A1 | 4/2009 | Zhang |
| 2010/0057152 | A1 | 3/2010 | Kim et al. |
| 2010/0274149 | A1 | 10/2010 | Li et al. |
| 2011/0152957 | A1 | 6/2011 | Shaquer |
| 2012/0035489 | A1 | 2/2012 | Dong et al. |
| 2012/0101541 | A1 | 4/2012 | Corbucci et al. |
| 2012/0238891 | A1 | 9/2012 | Sarkar et al. |
| 2012/0238892 | A1 | 9/2012 | Sarkar |
| 2013/0150911 | A1 | 6/2013 | Perschbacher et al. |
| 2016/0045125 | A1 | 2/2016 | Krueger et al. |
| 2016/0287115 | A1 | 10/2016 | Perschbacher et al. |
| 2017/0127965 | A1 | 5/2017 | Krueger et al. |
| 2018/0256053 | A1 | 9/2018 | Perschbacher et al. |

FOREIGN PATENT DOCUMENTS

| | | |
|---|---|---|
| CN | 106659407 A | 5/2017 |
| CN | 107529988 A | 1/2018 |
| EP | 2407097 A1 | 1/2012 |
| JP | 2004524074 A | 8/2004 |
| JP | 2006524106 A | 10/2006 |
| JP | 2008539015 A | 11/2008 |
| JP | 2009089883 A | 4/2009 |
| JP | 2013535236 A | 9/2013 |
| JP | 2017527356 A | 9/2017 |
| JP | 2018511400 A | 4/2018 |
| JP | 6434129 B2 | 11/2018 |
| JP | 6525461 B2 | 5/2019 |
| WO | WO-2006118852 A2 | 11/2006 |
| WO | WO-2013020710 A1 | 2/2013 |
| WO | WO-2016025704 A1 | 2/2016 |
| WO | WO-2016160674 A1 | 10/2016 |
| WO | WO-2017079245 A1 | 5/2017 |

OTHER PUBLICATIONS

"U.S. Appl. No. 14/825,669, Advisory Action dated May 3, 2017", 3 pgs.

"U.S. Appl. No. 14/825,669, Final Office Action dated Mar. 9, 2017", 13 pgs.

"U.S. Appl. No. 14/825,669, Non Final Office Action dated Jun. 23, 2017", 9 pgs.

"U.S. Appl. No. 14/825,669, Non Final Office Action dated Sep. 27, 2016", 9 pgs.

"U.S. Appl. No. 14/825,669, Response filed Jun. 8, 2017 to Final Office Action dated Mar. 9, 2017", 14 pgs.

"U.S. Appl. No. 15/082,440, Corrected Notice of Allowance dated Feb. 9, 2018", 5 pgs.

"U.S. Appl. No. 15/082,440, Examiner Interview Summary dated Sep. 6, 2017", 2 pgs.

"U.S. Appl. No. 15/082,440, Non Final Office Action dated Jun. 21, 2017", 9 pgs.

"U.S. Appl. No. 15/082,440, Notice of Allowance dated Jun. 18, 2018", 8 pgs.

"U.S. Appl. No. 15/082,440, Notice of Allowance dated Sep. 25, 2017", 10 pgs.

"U.S. Appl. No. 15/082,440, Response filed May 17, 2017 to Restriction Requirement dated Mar. 30, 2017", 9 pgs.

"U.S. Appl. No. 15/082,440, Response filed Sep. 5, 2017 to Non Final Office Action dated Jun. 21, 2017", 14 pgs.

"U.S. Appl. No. 15/082,440, Restriction Requirement dated Mar. 30, 2017", 7 pgs.

"Australian Application Serial No. 2015301633, First Examiners Report dated Sep. 7, 2017", 3 pgs.

"European Application Serial No. 15757059.9, Response filed Sep. 26, 2017 to Communication Pursuant to Rules 161(1) and 162 EPC mailed Mar. 21, 2017", 18 pgs.

"International Application Serial No. PCT/US2015/045042, International Preliminary Report on Patentability dated Feb. 23, 2017", 10 pgs.

"International Application Serial No. PCT/US2015/045042, International Search Report dated Oct. 27, 2015", 6 pgs.

"International Application Serial No. PCT/US2015/045042, Written Opinion dated Oct. 27, 2015", 9 pgs.

"International Application Serial No. PCT/US2016/024463, International Preliminary Report on Patentability dated Oct. 12, 2017", 8 pgs.

"International Application Serial No. PCT/US2016/024463, International Search Report dated Jun. 17, 2016", 6 pgs.

"International Application Serial No. PCT/US2016/024463, Written Opinion dated Jun. 17, 2016", 6 pgs.

Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.

Esperer, et al., "Cardiac arrhythmias imprint specific signatures on Lorenz plots", Ann Noninvasive Electrocardiol, (2008), 44-60 pgs.

Tateno, K, et al., "Automatic detection of atrial fibrillation using the coefficient of variation and density histograms of RR and RR intervals", Medical and Biological Engineering and Computing, vol. 39, No. 6,, (Nov. 1, 2011), 664-671.

"U.S. Appl. No. 14/825,669, Appeal Brief filed Dec. 26, 2017", 17 pgs.

"Australian Application Serial No. 2015301633, Response filed Mar. 21, 2018 to First Examiners Report dated Sep. 7, 2017", 14 pgs.

"European Application Serial No. 16715709.8, Response filed Jun. 27, 2018 to Communication Pursuant to Rules 161(1) and 162 EPC mailed Dec. 7, 2017", 28 pgs.

"International Application Serial No. PCT/US2016/060050, International Search Report dated Feb. 6, 2017", 4 pgs.

(56) References Cited

OTHER PUBLICATIONS

"International Application Serial No. PCT/US2016/060050, Written Opinion dated Feb. 6, 2017", 5 pgs.

"Japanese Application Serial No. 2017-508064, Office Action dated Mar. 6, 2018", With English Translation, 4 pgs.

"Japanese Application Serial No. 2017-508064, Response filed May 30, 2018 to Office Action dated Mar. 6, 2018", w/ English claims, 10 pgs.

Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.

"U.S. Appl. No. 15/341,565, Non Final Office Action dated Mar. 6, 2019", 12 pgs.

"U.S. Appl. No. 15/341,565, Response filed Dec. 10, 2018 to Restriction Requirement dated Oct. 15, 2018", 8 pgs.

"U.S. Appl. No. 15/341,565, Restriction Requirement dated Oct. 15, 2018", 6 pgs.

"Japanese Application Serial No. 2017-550731, Notification of Reasons for Refusal dated Dec. 18, 2018", w/ English summary, 6 pgs.

"Japanese Application Serial No. 2017-550731, Response filed Nov. 28, 2018 to Office Action dated Sep. 4, 2018", w/ English claims, 8 pgs.

"U.S. Appl. No. 15/341,565, Response filed Jun. 6, 2019 to Non Final Office Action dated Mar. 6, 2019", 10 pgs.

"Chinese Application Serial No. 201580047246.7, Office Action dated Mar. 6, 2019", w/ English Translation, 19 pgs.

"Japanese Application Serial No. 2017-550731, Response filed Mar. 15, 2019 to Notification of Reasons for Refusal dated Dec. 18, 2018", w/ English claims, 6 pgs.

"Chinese Application Serial No. 201580047246.7, Response Filed Jul. 22, 2019 to Office Action dated Mar. 6, 2019", w/English Claims, 17 pgs.

"U.S. Appl. No. 15/341,565, Notice of Allowance dated Jul. 26, 2019", 8 pgs.

| HRDI \ HRDI_HR | 0 | 30 | 40 | 50 | 60 | 70 | 80 | 90 | 100 | 110 | 120 | 130 | 140 | 150 | 160 | 170 | 180 | 190 | 200 |
|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | 0 |
| 0.05 | 0 | 0 | 0 | 0 | 0 | 0 | 0 | 0 | 0 | 0 | 0 | 0 | 0 | 0 | 0 | 0 | 0 | 0 | 0 |
| 0.1 | 0 | 0 | 0 | 0 | 0 | 0 | 0 | 0 | 0 | 0 | 0 | 0 | 0 | 0 | 0 | 0 | 0 | 0 | 0 |
| 0.15 | 0 | 0 | 0 | 0 | 0 | 0 | 0 | 0 | 0 | 0 | 0 | 0 | 0 | 0 | 0 | 0 | 0 | 0 | 0 |
| 0.2 | 0 | 0 | 0 | 1 | 0 | 0 | 0 | 0 | 0 | 0 | 0 | 0 | 0 | 0 | 0 | 0 | 0 | 0 | 0 |
| 0.25 | 0 | 0 | 0 | 0 | 1 | 1 | 2 | 0 | 0 | 0 | 0 | 0 | 0 | 0 | 0 | 0 | 0 | 0 | 0 |
| 0.3 | 0 | 0 | 0 | 1 | 4 | 2 | 2 | 0 | 0 | 0 | 0 | 0 | 0 | 0 | 0 | 0 | 0 | 0 | 0 |
| 0.35 | 0 | 0 | 0 | 0 | 2 | 2 | 4 | 1 | 0 | 0 | 0 | 0 | 0 | 0 | 0 | 0 | 0 | 0 | 0 |
| 0.4 | 0 | 0 | 0 | 4 | 7 | 5 | 4 | 0 | 1 | 0 | 0 | 0 | 0 | 0 | 0 | 0 | 0 | 0 | 0 |
| 0.45 | 0 | 0 | 0 | 5 | 14 | 10 | 6 | 2 | 0 | 0 | 0 | 0 | 0 | 0 | 0 | 0 | 0 | 0 | 0 |
| 0.5 | 0 | 0 | 0 | 4 | 16 | 5 | 5 | 2 | 0 | 0 | 0 | 0 | 0 | 0 | 0 | 0 | 0 | 0 | 0 |
| 0.55 | 0 | 0 | 0 | 4 | 10 | 5 | 6 | 2 | 0 | 0 | 0 | 0 | 0 | 0 | 0 | 0 | 0 | 0 | 0 |
| 0.6 | 0 | 0 | 0 | 3 | 13 | 6 | 8 | 0 | 0 | 0 | 0 | 0 | 0 | 0 | 0 | 0 | 0 | 0 | 0 |
| 0.65 | 0 | 0 | 0 | 5 | 10 | 4 | 10 | 1 | 0 | 0 | 0 | 0 | 0 | 0 | 0 | 0 | 0 | 0 | 0 |
| 0.7 | 0 | 0 | 0 | 6 | 11 | 1 | 7 | 2 | 0 | 0 | 0 | 0 | 0 | 0 | 0 | 0 | 0 | 0 | 0 |
| 0.75 | 0 | 0 | 0 | 12 | 8 | 4 | 3 | 0 | 0 | 0 | 0 | 0 | 0 | 0 | 0 | 0 | 0 | 0 | 0 |
| 0.8 | 0 | 0 | 0 | 7 | 9 | 8 | 6 | 0 | 0 | 0 | 0 | 0 | 0 | 0 | 0 | 0 | 0 | 0 | 0 |
| 0.85 | 0 | 0 | 0 | 4 | 7 | 6 | 0 | 0 | 0 | 0 | 0 | 0 | 0 | 0 | 0 | 0 | 0 | 0 | 0 |
| 0.9 | 0 | 0 | 0 | 11 | 6 | 5 | 2 | 0 | 0 | 0 | 0 | 0 | 0 | 0 | 0 | 0 | 0 | 0 | 0 |
| 0.95 | 0 | 0 | 0 | 7 | 2 | 4 | 1 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 | 0 | 0 | 0 | 0 | 0 | 0 | 0 |

*FIG. 8*

| HRDI \ HRDI_HR | 0 | 30 | 40 | 50 | 60 | 70 | 80 | 90 | 100 | 110 | 120 | 130 | 140 | 150 | 160 | 170 | 180 | 190 | 200 |
|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | 0 |
| 0.05 | 0 | 0 | 0 | 0 | 0 | 0 | 0 | 0 | 0 | 0 | 0 | 0 | 0 | 0 | 0 | 0 | 0 | 0 | 0 |
| 0.1 | 0 | 0 | 0 | 0 | 0 | 0 | 0 | 0 | 0 | 0 | 0 | 0 | 2 | 1 | 1 | 2 | 0 | 0 | 0 |
| 0.15 | 0 | 0 | 0 | 0 | 2 | 1 | 2 | 0 | 0 | 0 | 0 | 3 | 0 | 5 | 7 | 9 | 1 | 0 | 0 |
| 0.2 | 0 | 0 | 0 | 0 | 0 | 2 | 2 | 2 | 2 | 0 | 0 | 4 | 4 | 2 | 2 | 1 | 0 | 0 | 0 |
| 0.25 | 0 | 0 | 0 | 0 | 2 | 3 | 1 | 0 | 0 | 0 | 0 | 0 | 0 | 0 | 0 | 0 | 0 | 0 | 0 |
| 0.3 | 0 | 0 | 0 | 0 | 0 | 0 | 0 | 0 | 0 | 0 | 1 | 1 | 0 | 0 | 0 | 0 | 0 | 0 | 0 |
| 0.35 | 0 | 0 | 0 | 0 | 0 | 0 | 0 | 0 | 0 | 0 | 0 | 1 | 1 | 0 | 0 | 0 | 0 | 0 | 0 |
| 0.4 | 0 | 0 | 0 | 0 | 0 | 0 | 0 | 0 | 1 | 0 | 0 | 0 | 0 | 0 | 0 | 0 | 0 | 0 | 0 |
| 0.45 | 0 | 0 | 0 | 0 | 1 | 0 | 0 | 0 | 0 | 0 | 0 | 0 | 0 | 0 | 0 | 0 | 0 | 0 | 0 |
| 0.5 | 0 | 0 | 0 | 0 | 2 | 0 | 0 | 0 | 0 | 0 | 0 | 0 | 0 | 0 | 0 | 0 | 0 | 0 | 0 |
| 0.55 | 0 | 0 | 0 | 0 | 0 | 0 | 0 | 0 | 0 | 0 | 0 | 0 | 0 | 0 | 0 | 0 | 0 | 0 | 0 |
| 0.6 | 0 | 0 | 0 | 0 | 0 | 0 | 0 | 0 | 0 | 0 | 0 | 0 | 0 | 0 | 0 | 0 | 0 | 0 | 0 |
| 0.65 | 0 | 0 | 0 | 0 | 0 | 0 | 0 | 0 | 0 | 0 | 0 | 0 | 0 | 0 | 0 | 0 | 0 | 0 | 0 |
| 0.7 | 0 | 0 | 0 | 0 | 0 | 0 | 0 | 0 | 0 | 0 | 0 | 0 | 0 | 0 | 0 | 0 | 0 | 0 | 0 |
| 0.75 | 0 | 0 | 0 | 0 | 0 | 0 | 0 | 0 | 0 | 0 | 0 | 0 | 0 | 0 | 0 | 0 | 0 | 0 | 0 |
| 0.8 | 0 | 0 | 0 | 0 | 0 | 0 | 0 | 0 | 0 | 0 | 0 | 0 | 0 | 0 | 0 | 0 | 0 | 0 | 0 |
| 0.85 | 0 | 0 | 0 | 0 | 0 | 0 | 0 | 0 | 0 | 0 | 0 | 0 | 0 | 0 | 0 | 0 | 0 | 0 | 0 |
| 0.9 | 0 | 0 | 0 | 0 | 0 | 0 | 0 | 0 | 0 | 0 | 0 | 0 | 0 | 0 | 0 | 0 | 0 | 0 | 0 |
| 0.95 | 0 | 0 | 0 | 0 | 0 | 0 | 0 | 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 | 0 | 0 | 0 | 0 | 0 | 0 | 0 | 0 |

*FIG. 9*

ATRIAL FIBRILLATION DETECTION

CLAIM OF PRIORITY

This application is a continuation of U.S. application Ser. No. 15/082,440, filed Mar. 28, 2016, now issued as U.S. Pat. No. 9,999,368, which claims the benefit of priority under 35 U.S.C. § 119(e) of U.S. Provisional Patent Application Ser. No. 62/142,184, filed on Apr. 2, 2015, each of which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs) and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest.

CFM devices can be implantable but in some situations may not include dedicated atrial sensing capability. Additionally, some diagnostic-only implantable, wearable, and handheld devices do not include dedicated atrial sensing capability. Patients with these types of devices may develop atrial arrhythmias, such as atrial fibrillation (AF) for example. This is especially true for heart failure patients who typically have a high incidence of AF. Knowledge that a specific patient is experiencing AF can be useful to physicians and clinicians for diagnostic purposes or to tailor performance of a medical device to that patient's needs to provide the most effective patient therapy.

OVERVIEW

It can be desirable for ambulatory medical devices to correctly detect and identify cardiac arrhythmias. This can help to provide the most effective device-based therapy or non-device based therapy for the patient. The present subject matter relates to improving detection of atrial fibrillation.

One example system of the present subject matter can include a sensing circuit configured to generate a sensed physiological signal representative of cardiac activity of a subject, and one or more arrhythmia detection circuits. The arrhythmia detection circuits can be configured to monitor information corresponding to ventricular depolarization (V-V) intervals using the sensed physiological signal, generate a heart rate distribution using the information corresponding to the V-V intervals, determine a characteristic of a heart rate density index (HRDI), and generate an indication of atrial fibrillation (AF) using the heart rate mode and the characteristic of the HRDI.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

FIG. 8 shows heart rate mode data and heart rate density index data for a population of patients in normal sinus rhythm.

FIG. 9 shows heart rate mode data and heart rate density index data for a population of patients in atrial fibrillation.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
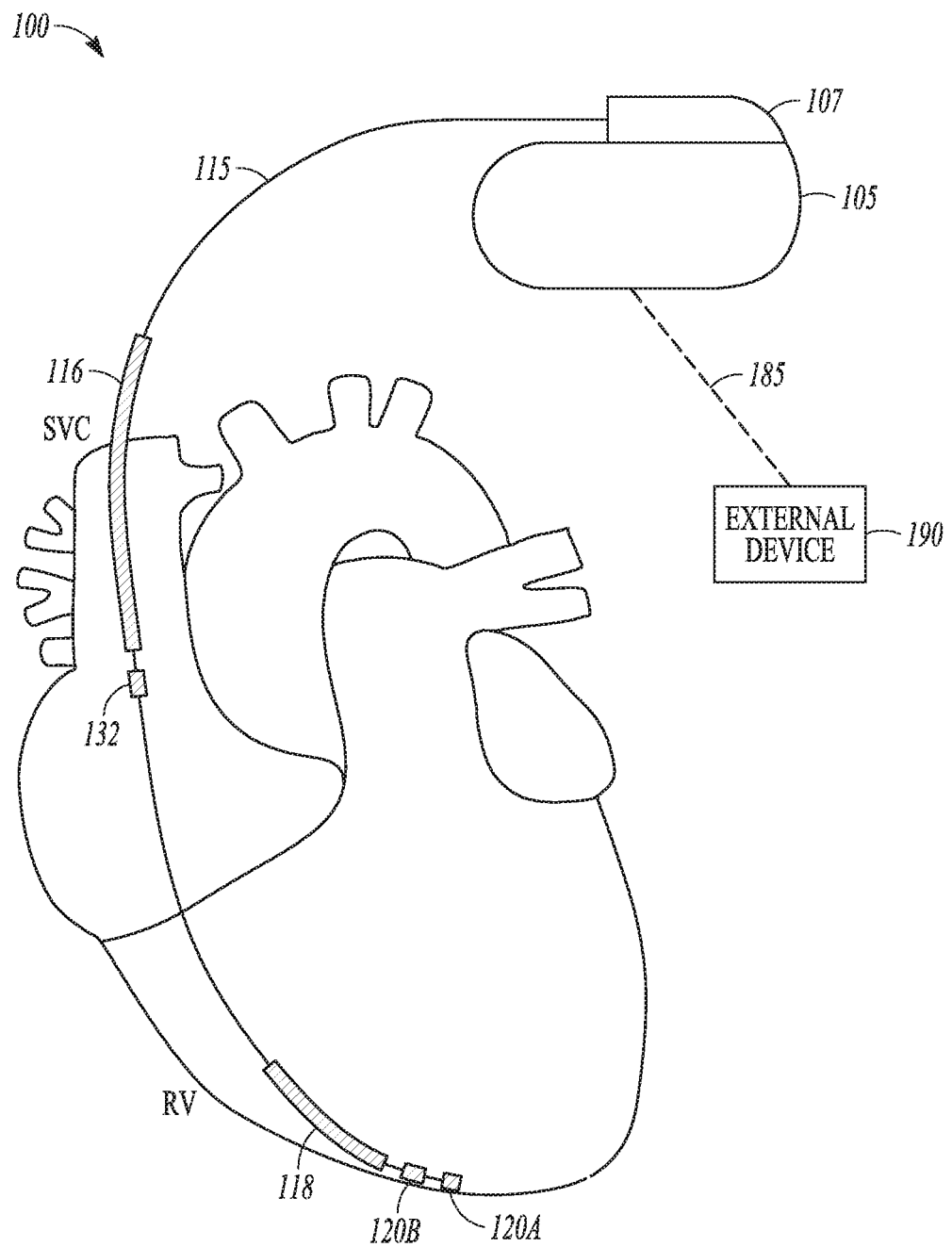
FIG. 1 is an illustration of an example of portions of a medical device system that includes an IMD.

FIG. 1 is an illustration of an example of portions of a system 100 that includes an IMD 105. Examples of the IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an MD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The IMD 105 includes a sense amplifier circuit to provide amplification or filtering of the sensed signal. Sensing and pacing allows the IMD 105 to adjust timing of the heart chamber contractions.

Some IMDs, such as shown in FIG. 1, may not include any electrodes for sensing electrical activity in an atrium. For example, the IMD 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis).

An IMD may be a diagnostic-only device and not provide electrical therapy to the patient. Such a device may include a combination of the RV tip electrode 120A, RV ring electrode 120B, or the electrode formed on the can of IMD 105 allow for sensing ventricular depolarizations. Note that the specific arrangement of leads and electrodes are shown the illustrated example of FIG. 1 is intended to be non-limiting.

Figure 2:
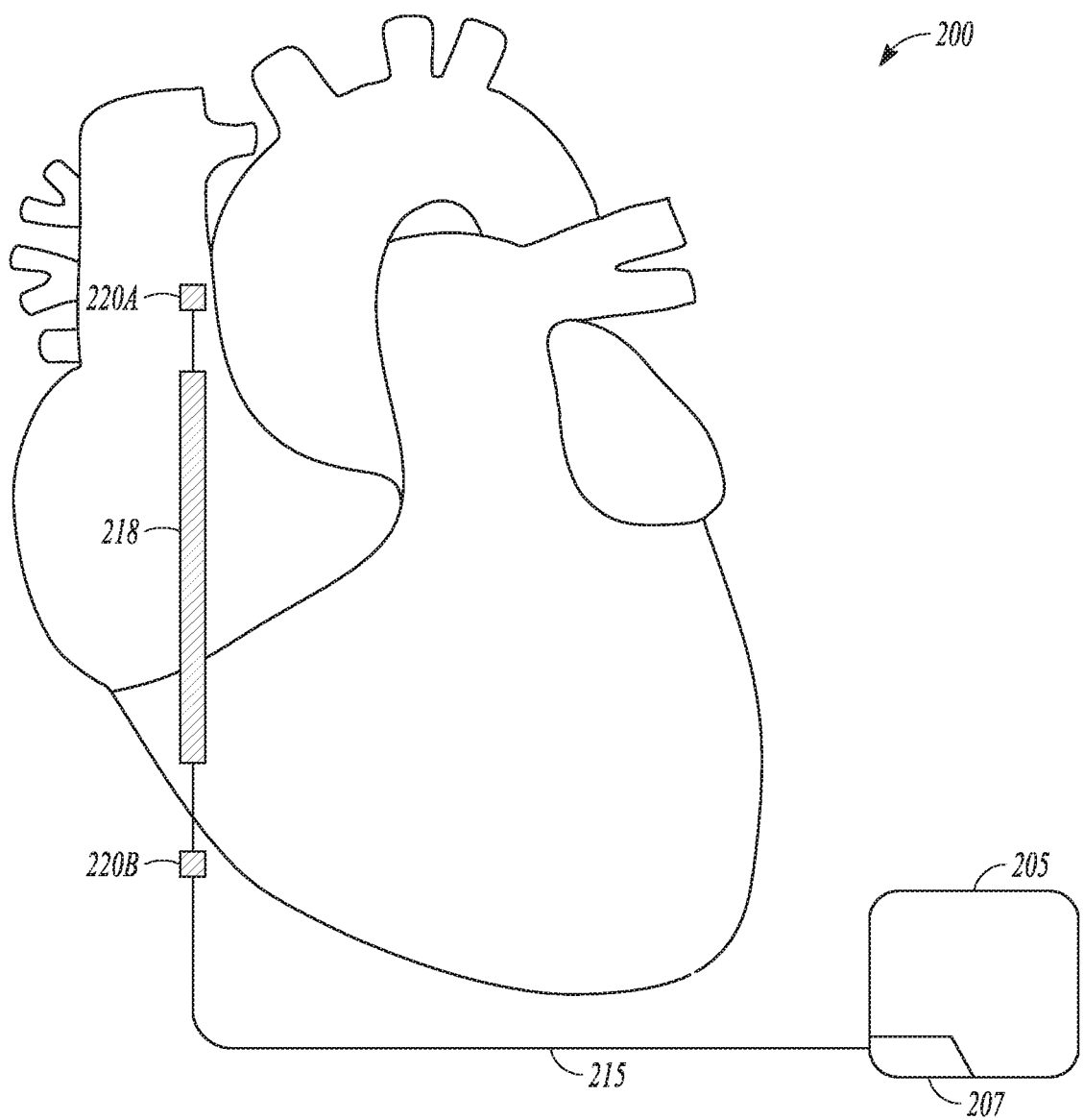
FIGS. 2 and 3 are illustrations of further examples of an IMD.

FIG. 2 is an illustration of another example of portions of a system 200 that includes an S-ICU 205. The S-ICD 205 is implantable subcutaneously and includes a lead 215. The lead 215 is also implanted subcutaneously and the proximal end of the lead 215 is coupled to a header connector 207. The lead 215 can include electrode 220A and electrode 220B to sense ventricular depolarization (e.g., using far-field sensing), but in the example illustrated, the lead does not include any electrodes that directly contact the heart. The lead 215 includes a defibrillation electrode 218 that may be a coil electrode. The S-ICD 205 may provide one or more of cardioversion therapy and defibrillation high energy shock therapy to the heart using the defibrillation electrode 218 and an electrode formed on the can of the S-ICD 205. In some examples, the S-ICD 205 may also provide pacing pulses for anti-tachycardia therapy or bradycardia therapy. Note that direct atrial sensing is not provided in the arrangement of the electrodes.

Figure 3:
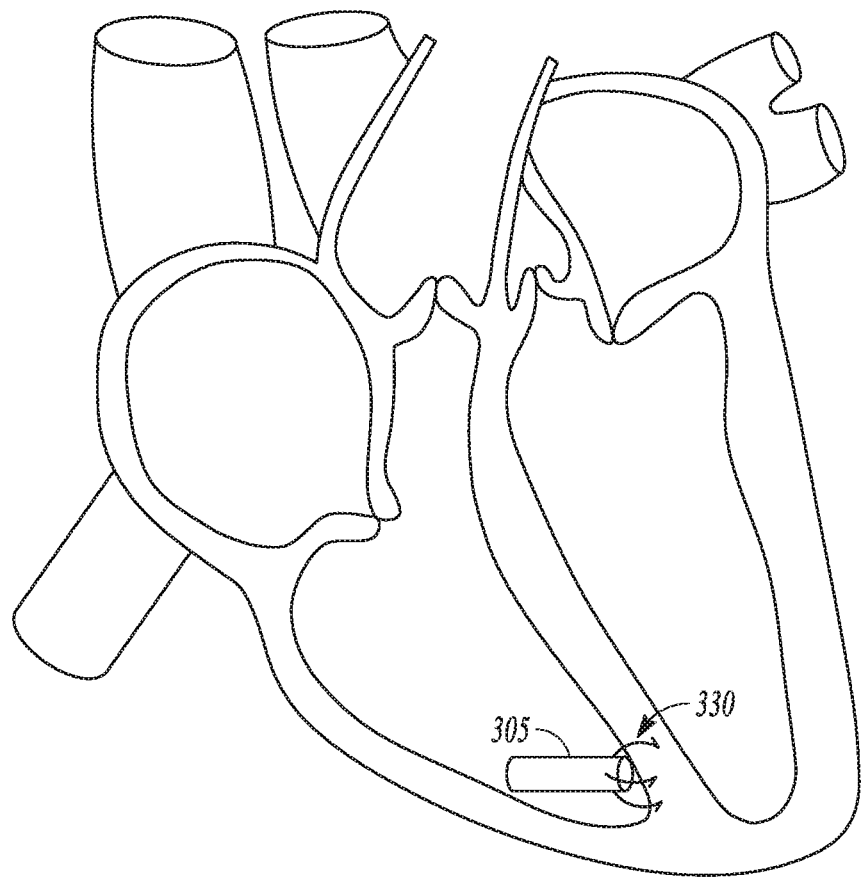

FIG. 3 is an illustration of an example of an IMD that is leadless. In the example shown, the IMD is a leadless pacemaker 305. The leadless pacemaker 305 is shown positioned at the endocardium within a ventricular chamber, but the leadless pacemaker 305 may be positioned at other locations of the heart. The leadless pacemaker 305 example has a cylindrical or bullet shape housing and may include one or more electrodes arranged along the cylindrical housing to sense electrical signals of the heart and/or provide electrical stimulation for pacing the heart. The one or more electrodes may be used for communication. The leadless pacemaker 305 may include a mechanism 330 to fix the pacemaker to the myocardium. Examples of the fixation mechanism can include one or more tines, one or more barbed tines, and one or more helix-shaped fixation mechanisms. Direct atrial sensing may not be provided by the electrodes for the device placement shown in the example.

Other examples of an IMD include an implantable loop recorder (ILR), a diagnostic device without leads in the heart, and a neurostimulator (including but not limited to vagus nerve stimulators, baroreceptor stimulators, and spinal cord stimulators), or other IMD. These types of devices may not include an electrode positioned in the atrium.

Figure 4:
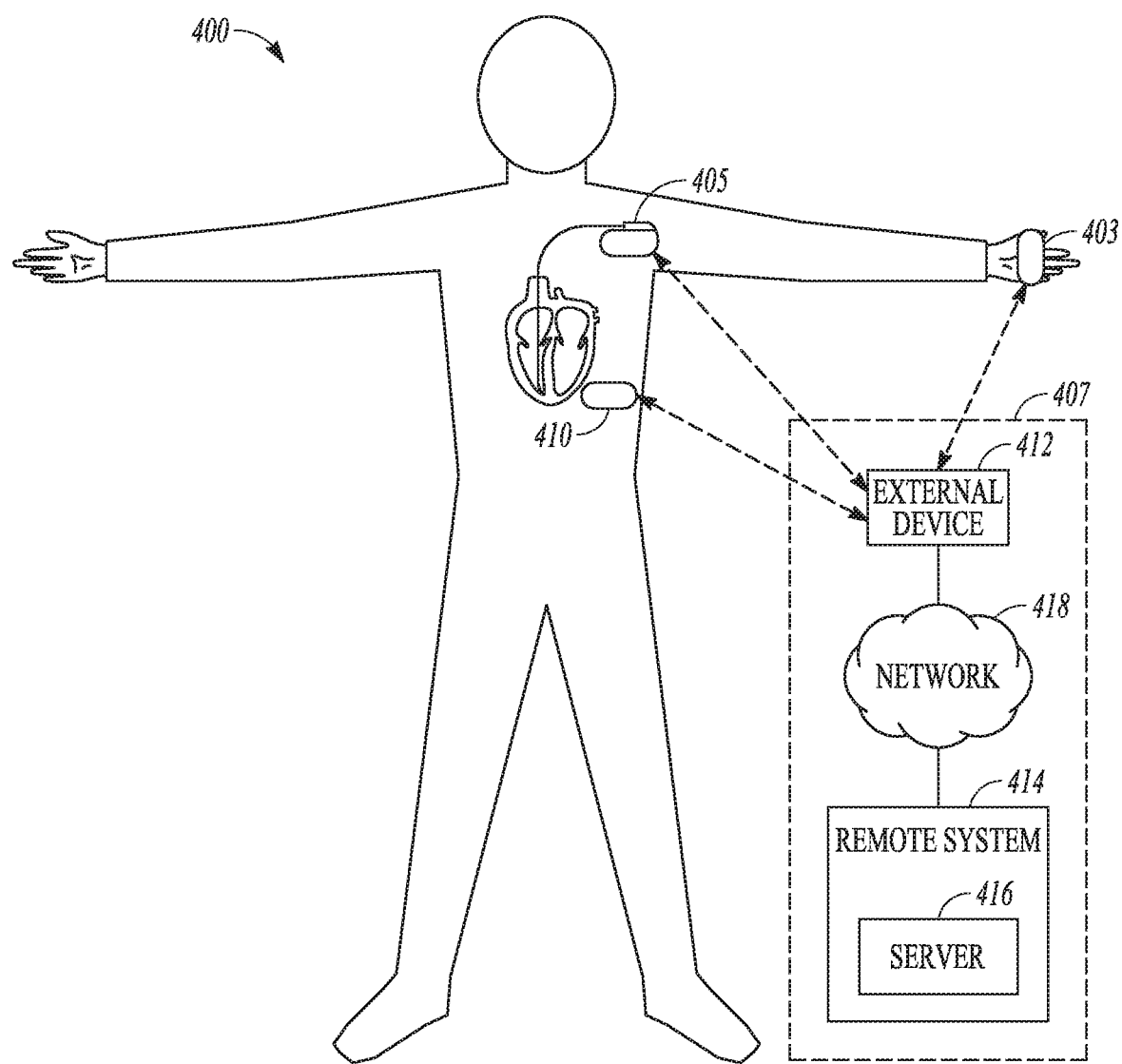
FIG. 4 is an illustration of portions of another example of a medical device system.

FIG. 4 is an illustration of portions of another example of a medical device system 400. The system 400 may include one or more ambulatory medical devices, such as a conventionally implantable or subcutaneously implantable medical device 405, a wearable medical device 410, or a handheld medical device 403. One or more of the medical devices can include a communication circuit (e.g., a telemetry circuit) to communicate the indication of AF to a communication system 407. The communication system 407 can include an external communication device 412 and a remote system 414 that communicates with the external communication device 412 via a network 418 (e.g., the internet, a proprietary computer network, or a cellular phone network). The remote system 414 may include a server 416 remotely located from the external communication device 412 and the subject to perform patient management functions. The external communication device 412 may include a programmer to program therapy parameters of a device-based therapy provided by the implantable medical device. One or both of the external communication device 412 and the remote system 414 may include a display to present the indication of AF to a user, such as a clinician.

Figure 5:
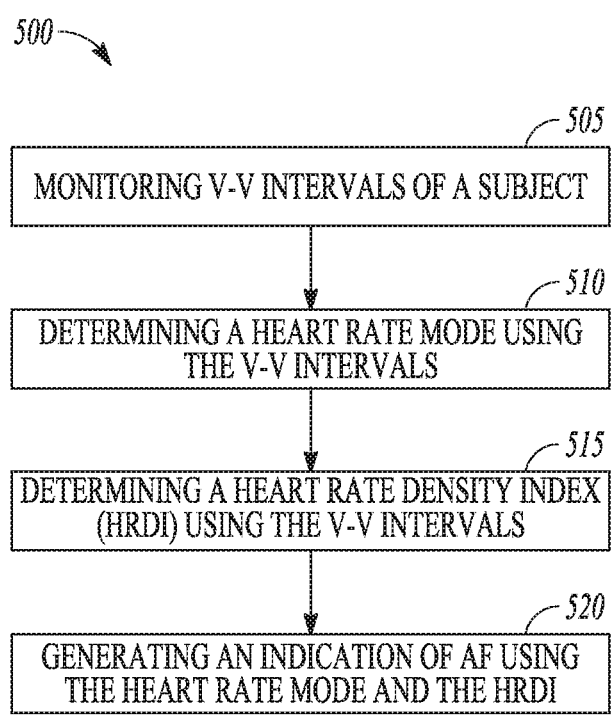
FIG. 5 shows a flow diagram of an example of a method of operating an ambulatory medical device.

FIG. 5 is a flow diagram of an example of a method 500 of operating an ambulatory medical device. The method 500 provides for detecting AF using the ambulatory medical even though the ambulatory medical device may not include electrodes and sensing circuitry to implement direct atrial sensing.

At 505, information corresponding to ventricular depolarization intervals (or V-V intervals) of a subject are monitored. The intervals could be monitored in beats per minute (bpm) or in time (e.g., milliseconds). One skilled in the art would understand, upon reading this document, that heart rate can be determined using intervals between cardiac depolarization and the terms heart rate and interval can be used interchangeably in the methods described. The depolarization intervals may be sensed at the right ventricle or left ventricle. The information may include sampled values of the V-V intervals. A distribution of the V-V intervals is determined.

Figure 6:
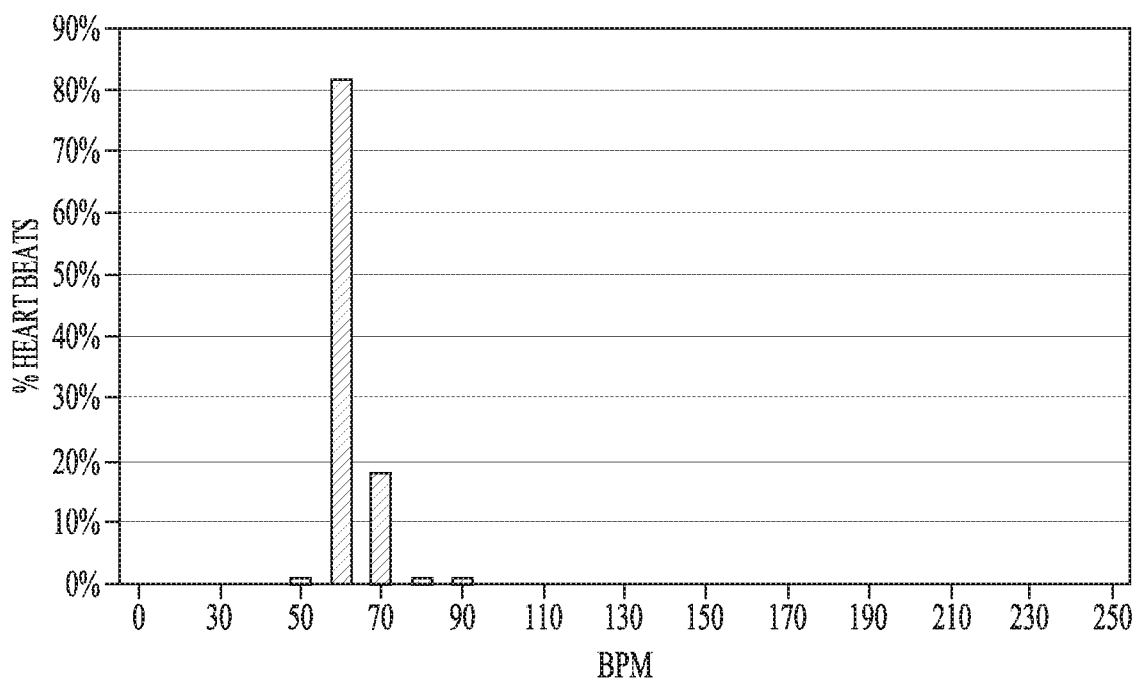
FIG. 6 shows a graph of an example of a heart rate distribution for a patient in normal sinus rhythm.

In some examples as shown at 510, a heart rate mode is determined using the V-V intervals. Heart rate mode refers to the heart rate that appears most often in a distribution of heart rates or heartbeat intervals. FIG. 6 shows a graph of an example of a heart rate distribution for normal sinus rhythm (NSR). Most of the samples of the distribution are located between approximately 50 bpm and 90 bpm. The mode for the distribution is approximately 60 bpm because that is the heart rate that appears most often in the distribution.

Returning to FIG. 5 at 515, a heart rate density index (HRDI) is determined using the V-V intervals. In some examples, HRDI can be a portion of samples of the V-V interval distribution corresponding to a V-V interval occurring most often in the distribution. In some examples, HRDI can be the portion of the V-V intervals in the distribution having the heart rate mode. In certain variations, HRDI is expressed as a fraction (e.g., a percentage) of the intervals. In the example of FIG. 6, the HRDI is 81% corresponding to the heart rate mode of 60 bpm.

Figure 7:
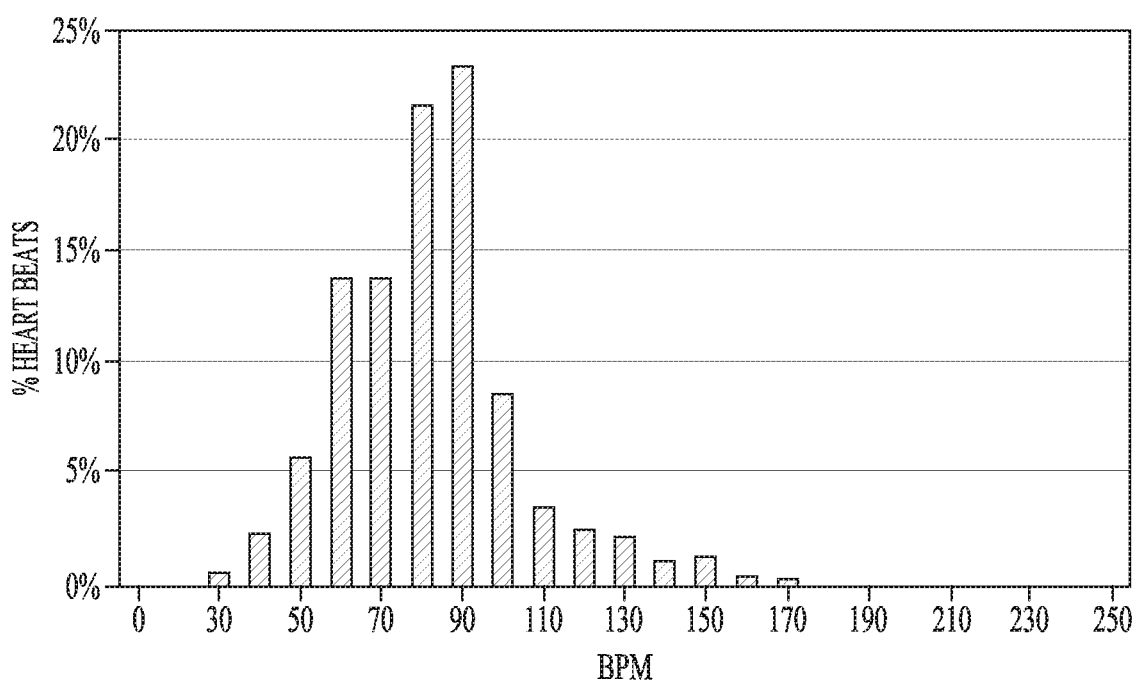
FIG. 7 shows a graph of an example of a heart rate distribution for a patient in atrial fibrillation.

At 520 of FIG. 5, an indication of AF is generated using the heart rate mode and the HRDI. FIG. 7 shows a graph of an example of a heart rate distribution for a patient in AF. It can be seen that heart rate is less regular in AF than in NSR. In the example of FIG. 7, the heart rate mode is 90 bpm and the HRDI is approximately 23%. The values of heart rate mode and HRDI can be measured only using V-V intervals. In this way, AF can be detected without including dedicated atrial sensing in the ambulatory medical device.

FIG. 8 shows heart rate mode data and HRDI data for a population of patients in NSR. It can be seen in FIG. 8 that data is mostly included in the unshaded area above an HRDI of 25% and a heart rate mode below 100 bpm. FIG. 9 shows heart rate mode data and HRDI data for a population of patients in AF. It can be seen in FIG. 9 that data is mostly included in the unshaded area below an HRDI of 25% and a heart rate mode above 100 bpm.

In some variations, HRDI is determined using the shape of the heart rate distributions. For instance, the HRDI may be a measure of one or more of the skew, the kurtosis, and variance of the heart rate distributions of FIGS. 6 and 7.

According to some examples, the HRDI can be compared to a specified HRDI threshold value. AF is detected when the HRDI satisfies the specified HRDI threshold value. In some examples, the HRDI can be compared to the specified HRDI threshold value and the heart rate mode can be compared to a heart rate mode threshold value. An indication of AF can be generated when the determined heart rate mode satisfies the heart rate mode threshold value or the determined HRDI satisfies the HRDI threshold value. The "or" is intended to be nonexclusive. Thus in the examples of FIG. 8 and FIG. 9, the indication of AF can be generated for a patient when the heart rate mode for heart rate samples for the patient is greater than 100 bpm, when the HRDI for the samples is less than 25%, or both the heart rate mode is greater than 100 bpm and the HRDI is less than 25% for the heart rate samples.

Figure 10:
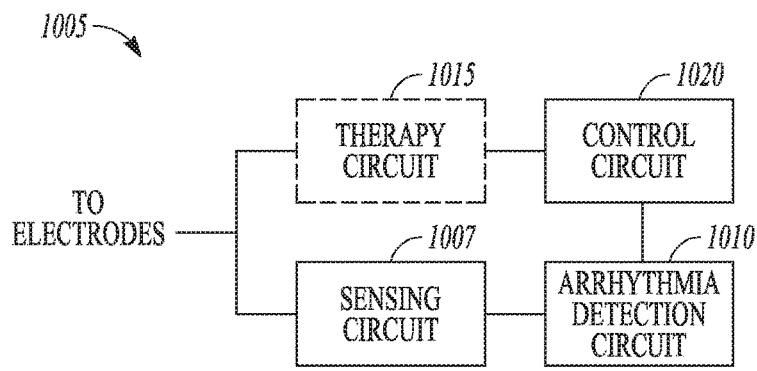
FIG. 10 shows a block diagram of portions of an example of an ambulatory medical device.

FIG. 10 shows a block diagram of portions of an example of an ambulatory medical device. The device 1005 includes a sensing circuit 1007 and an arrhythmia detection circuit 1010. The sensing circuit 1007 generates a sensed physiological signal representative of cardiac activity of a subject. In certain examples, the sensing circuit 1007 is to be electrically coupled to an implantable electrode included in a lead arranged for placement of the implantable in a heart chamber. In certain examples, the sensing circuit 1007 is to be electrically coupled to an implantable electrode included in a leadless implantable medical device. In certain examples, the sensing circuit 1007 is to be electrically coupled to an implantable electrode that is configured to sense cardiac signals without direct cardiac contact with the subject (e.g., a subcutaneously implantable electrode). In certain examples, the sensing circuit 1007 and the arrhythmia detection circuit 1010 are included in a wearable device or a handheld device.

In certain examples, the sensing circuit 1007 is a heart sound sensing circuit (e.g., an accelerometer). Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound signal can be an electrical signal representative of one or more heart sounds produced by the heart sound sensor circuit. The heart sound signal can be used to determine heart rate and depolarization intervals.

The arrhythmia detection circuit 1010 may include a microprocessor, a digital signal processor, application specific integrated circuit (ASIC), or other type of processor, interpreting or executing instructions included in software or firmware. The arrhythmia detection circuit 1010 is able to determine ventricular depolarization (V-V) intervals using the sensed physiological signal and monitor the intervals. The arrhythmia detection circuit 1010 may include a peak detector circuit to detect R-waves in the sensed physiological signal to determine V-V intervals. The arrhythmia detection circuit 1010 may sample the V-V intervals and store the samples in memory.

The arrhythmia detection circuit 1010 may determine a distribution of the V-V intervals such as by binning intervals using memory and determining the number of intervals per bin. From the V-V interval distribution, the arrhythmia detection circuit 1010 determines an HRDI. In some examples, the arrhythmia detection circuit 1010 determines the HRDI as a portion of samples of the V-V interval distribution corresponding to a V-V interval occurring most often in the distribution. The arrhythmia detection circuit 1010 generates an indication of AF using the HRDI. In some examples the arrhythmia detection circuit 1010 compares the HRDI to a specified HRDI threshold value and generates the indication of AF when the determined HRDI satisfies the threshold value.

In some examples, the arrhythmia detection circuit 1010 determines a heart rate mode using the V-V intervals. The arrhythmia detection circuit 1010 generates an indication of AF using the heart rate mode and the HRDI. In certain examples, the arrhythmia detection circuit 1010 generates an indication of AF when the determined heart rate mode satisfies a specified heart rate mode threshold value or the determined HRDI satisfies a specified HRDI threshold value. The heart rate mode and the HRDI may be determined for a specified duration of time. In certain variations, the heart rate mode and the HRDI may be determined for a physiological signal sensed and stored in a memory of the device 1000.

According to some examples, the determination of AF using heart rate mode and HRDI can be combined with other methods of determining AF. For instance, in some examples the arrhythmia detection circuit 1010 may combine a determination of AF using ventricular interval dispersion in combination with the determination of AF using heart rate mode and HRDI.

Figure 11:
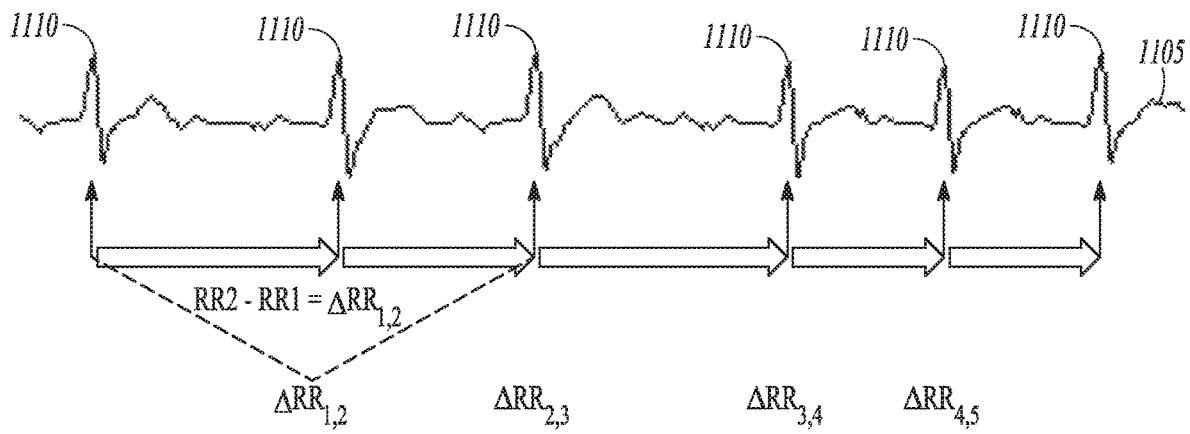
FIG. 11 shows a representation of an example of a sensed physiological signal.

FIG. 11 shows a representation of a sensed physiological signal 1105. The signal is shown having a number of R-waves 1110. The V-V intervals can be determined as intervals between R-waves. RR1 in the Figure refers to the first interval between the first two R-waves; RR2 is the second interval between the second R-wave and the third R-wave, and so on. Differences between the V-V intervals are referred to $\Delta RR_{1,2}$ (e.g., the difference between the RR2 and RR1), $\Delta RR_{2,3}$, and so on.

Figure 12:
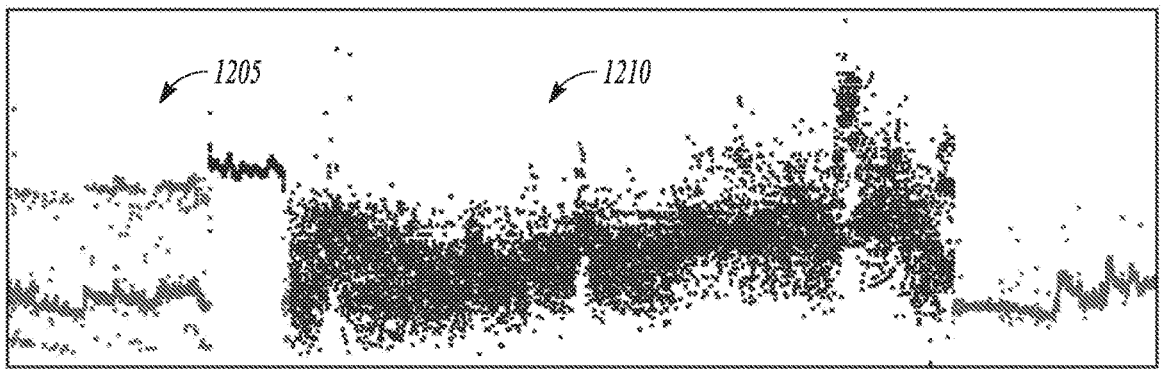
FIG. 12 shows a representation of another example of a sensed physiological signal that includes normal sinus rhythm and atrial fibrillation.

FIG. 12 shows an example of a sensed physiological signal having a first region 1205 corresponding to NSR and a second region 1210 corresponding to AF. In the NSR region, the V-V intervals will be more regular and the differences in the V-V intervals will be small. In the AF region, the V-V intervals will be more scattered and the values of the differences in the V-V intervals will be more varied than for NSR.

Figure 13:
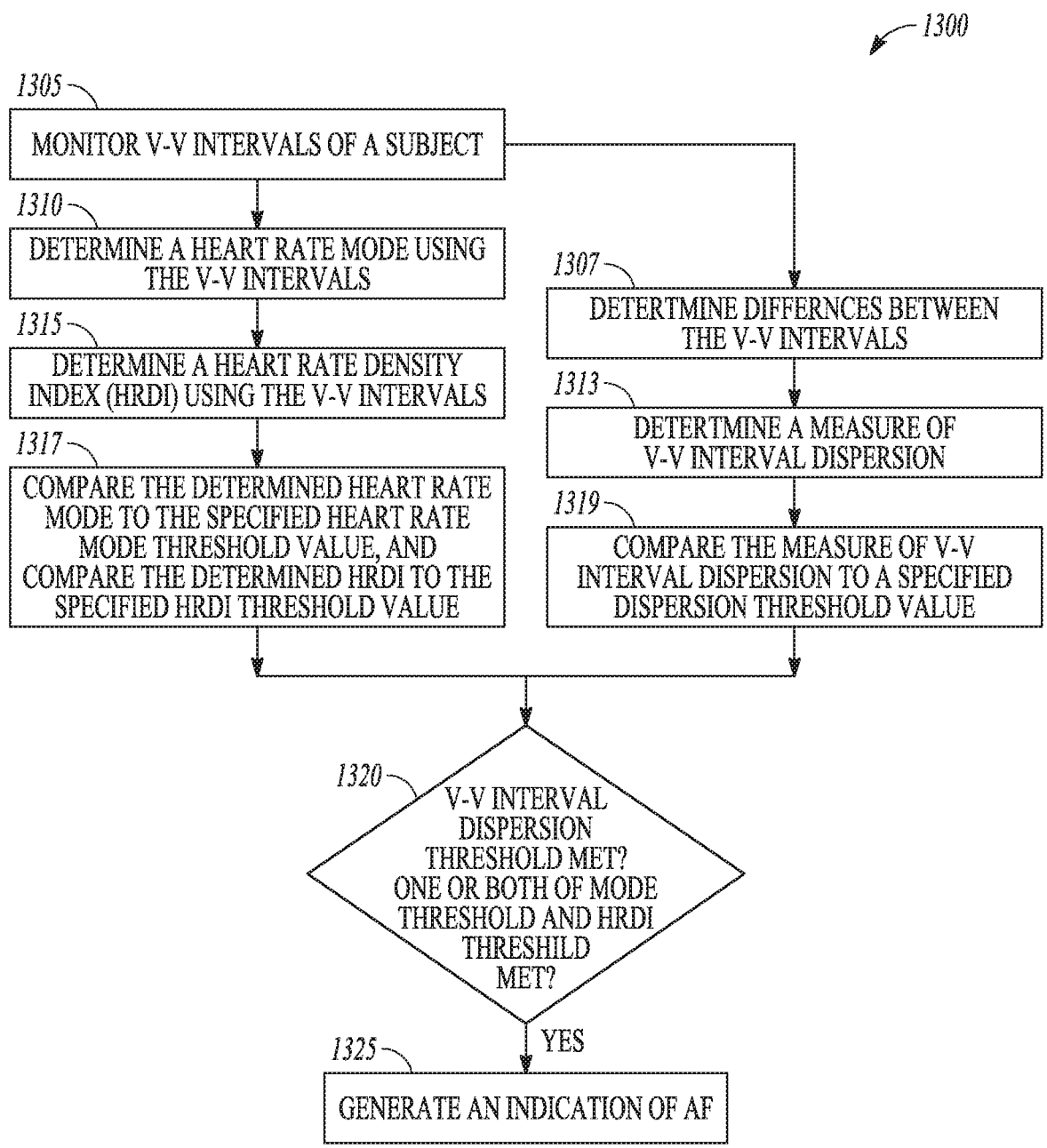
FIG. 13 is a flow diagram of another example of a method of operating an ambulatory medical device.

FIG. 13 is a flow diagram of another example of a method 1300 of operating an ambulatory medical device. Blocks 1305, 1310, and 1315 are performed to determine heart rate mode and HRDI as described regarding blocks 505, 510, and 515 of FIG. 5. At 1307, the arrhythmia detection circuit 1010 of FIG. 10 determines differences between the monitored V-V intervals, and at 1313 determines a measure of V-V interval dispersion using the determined V-V interval differences. In some examples, the measure of V-V interval dispersion includes a determined variance of the determined interval differences. To detect AF, the arrhythmia detection circuit 1010 uses the measure of ventricular interval dispersion, the determined heart rate mode, and the determined HRDI.

At 1317, the arrhythmia detection circuit 1010 compares the determined heart rate mode to the specified heart rate mode threshold value, and compares the determined HRDI to the specified HRDI threshold value. At 1319, the arrhythmia detection circuit 1010 compares the measure of V-V interval dispersion to a specified dispersion threshold value (e.g., a measure of V-V interval variance is compared to a specified variance threshold value). At 1320, the arrhythmia detection circuit 1010 determines whether both of i) the determined measure of V-V dispersion satisfies the specified dispersion threshold value, and ii) the determined heart rate mode satisfies the specified heart rate mode threshold value or the determined HRDI satisfies the specified HRDI threshold value. If so, at 1325 the arrhythmia detection circuit 1010 generates the indication of AF. In other words, the arrhythmia detection circuit 1010 generates the indication of AF when the criteria for both methods of detecting AF are satisfied.

In certain examples, the arrhythmia detection circuit 1010 determines the measure of V-V interval dispersion over a duration of time different from a duration of time used to determine the heart rate mode and HRDI. In an illustrative example intended to be non-limiting, the arrhythmia detection circuit 101 may determine the measure of ventricular interval dispersion over a window of a specified number of cardiac cycles (e.g., 100-200 cardiac cycles) and determine heart mode and HRDI over a window of ten minutes.

AF can be detected using other measures of ventricular interval dispersion in combination with the method of heart rate mode and HDRI. In some examples, the arrhythmia detection circuit 1010 determines the differences in the V-V intervals and classifies the interval differences as one of stable, unstable, or unstable and random. In certain variations, the intervals are classified into a stable bin, an unstable bin, or an unstable-random bin.

An interval difference may be classified as stable when the interval difference is less than a specified threshold difference value from an immediately previous interval difference. An interval difference may be classified as unstable when the interval difference is more than the specified threshold difference value from the immediately previous interval difference, and classified as unstable-random when the magnitude of the interval difference is more than the specified threshold difference value from the immediately previous interval difference and the interval difference is a negative value, that satisfies a specified negative value threshold.

In certain examples, the threshold difference value is a value corresponding to less than a 10 bpm difference in rate between the two intervals. Thus, if RR2 in FIG. 11 is 1000 ms corresponding to 60 bpm, and RR1 is 857 ms corresponding to 70 bpm, the interval difference $\Delta RR_{1,2}$ is binned as stable. If RR1 is less than 857 ms, then the interval difference is binned as unstable. If RR2 is less than 857 ms and RR1 is equal to 1000 ms, the interval difference $\Delta RR_{1,2}$ is binned as unstable-random. In certain examples, interval differences are only considered for binning if the intervals used (e.g., interval RR1 and RR2) are included in a triplet of three ventricular beats that are longer than a specified minimum interval (e.g., an interval of 324 ms corresponding to a heart rate of 1.85 bpm).

Returning to the example of FIG. 12, more of the V-V interval differences will be stable in the NSR region. In the AF region, the number of unstable V-V interval differences and unstable-random V-V interval differences will increase relative to the number of stable V-V interval differences. The arrhythmia detection circuit 1010 may determine a first metric of ventricular interval difference distribution using a number of stable interval differences and a number of unstable interval differences. The first metric may include a first ratio determined using a number of stable interval differences and a number of unstable interval differences (e.g., first ratio=unstable/stable).

The arrhythmia detection circuit 1010 may determine a second metric of ventricular interval difference distribution using a determined portion of the interval differences that are unstable-random. The second metric may include a second ratio determined using a number of unstable-random interval differences and a sum including the number of stable interval differences and the number of unstable interval differences (e.g., second ratio=(unstable−random)/(stable+unstable)).

In the case where the first and second metrics are the ratios, the value of the first ratio will increase in the presence of AF because the number of instable interval differences will increase. The value of the second ratio will tend to increase in the presence of AF because the number of unstable-random interval differences will increase. The arrhythmia detection circuit 1010 compares the determined first ratio to a specified first ratio threshold value (e.g., a ratio value of 3) and compares the determined second ratio to a specified second ratio threshold value (e.g., a ratio value of 0.06 or 6%). The arrhythmia detection circuit 1010 generates the indication of AF when both of i) the first ratio satisfies the specified first ratio threshold value and the determined second ratio satisfies the specified second ratio threshold value, and ii) the determined heart rate mode satisfies the specified heart rate mode threshold value or the determined HRDI satisfies the specified HRDI threshold value.

If the device 1005 is a diagnostic only device (e.g., an ILR), the generated indication of AF may be stored as an event in memory and may be stored in association with a timestamp of when the AF is detected. If the device 1005 is therapeutic, the device 1005 may include a therapy circuit 1015 that can be coupled to electrodes to provide an anti-arrhythmic cardiac therapy to a subject, such as anti-arrhythmia pacing energy or high energy shock therapy such as cardioversion therapy or defibrillation therapy. The device 1005 may include a control circuit 1020 that initiates delivery of an anti-arrhythmic therapy in response to the generated indication of AF.

The different methods of detecting AF that are combined may have different strengths and weaknesses. The combining of the different methods can be made into a fuzzy detection approach by separately tuning the detection of the individual detection methods.

For instance, in the example of the ratios described previously, one or any combination of the specified first ratio threshold value, the specified second ratio threshold value, the specified heart rate mode threshold value, and the specified HRDI threshold value can be adjustable in the arrhythmia detection circuit 1010. In this way, one criterion to detect AF can be made more sensitive than the other criterion.

For instance, one or both of the specified first ratio threshold value and the specified second ratio threshold value can be tuned to be more sensitive to detection of AF than the specified heart rate mode threshold value and the specified HRDI threshold value. In an illustrative example intended to be non-limiting, the threshold value for the unstable/stable ratio can be lowered (e.g., from 3.0 to 2.7) to be more easily satisfied by detected cardiac events. The unstable-random ratio threshold can be maintained at a normal threshold value of 6%, the threshold can be maintained at 0.3, and the heart rate mode threshold can be maintained at 100 bpm.

Alternatively, one or both of the specified heart rate mode threshold value and the specified HRDI threshold value can be tuned to be more sensitive to detection of AF than the specified first ratio threshold value and the specified second ratio threshold value. As another illustrative example intended to be non-limiting, the threshold for HRDI can be increased from 0.25 to 0.30 to be more easily satisfied by detected cardiac events. The heart rate mode threshold value can be maintained at 100 bpm, the threshold value for the unstable/stable ratio can be can be maintained at 3, and the threshold value for the unstable-random ratio can be maintained at 6%.

Figure 14:
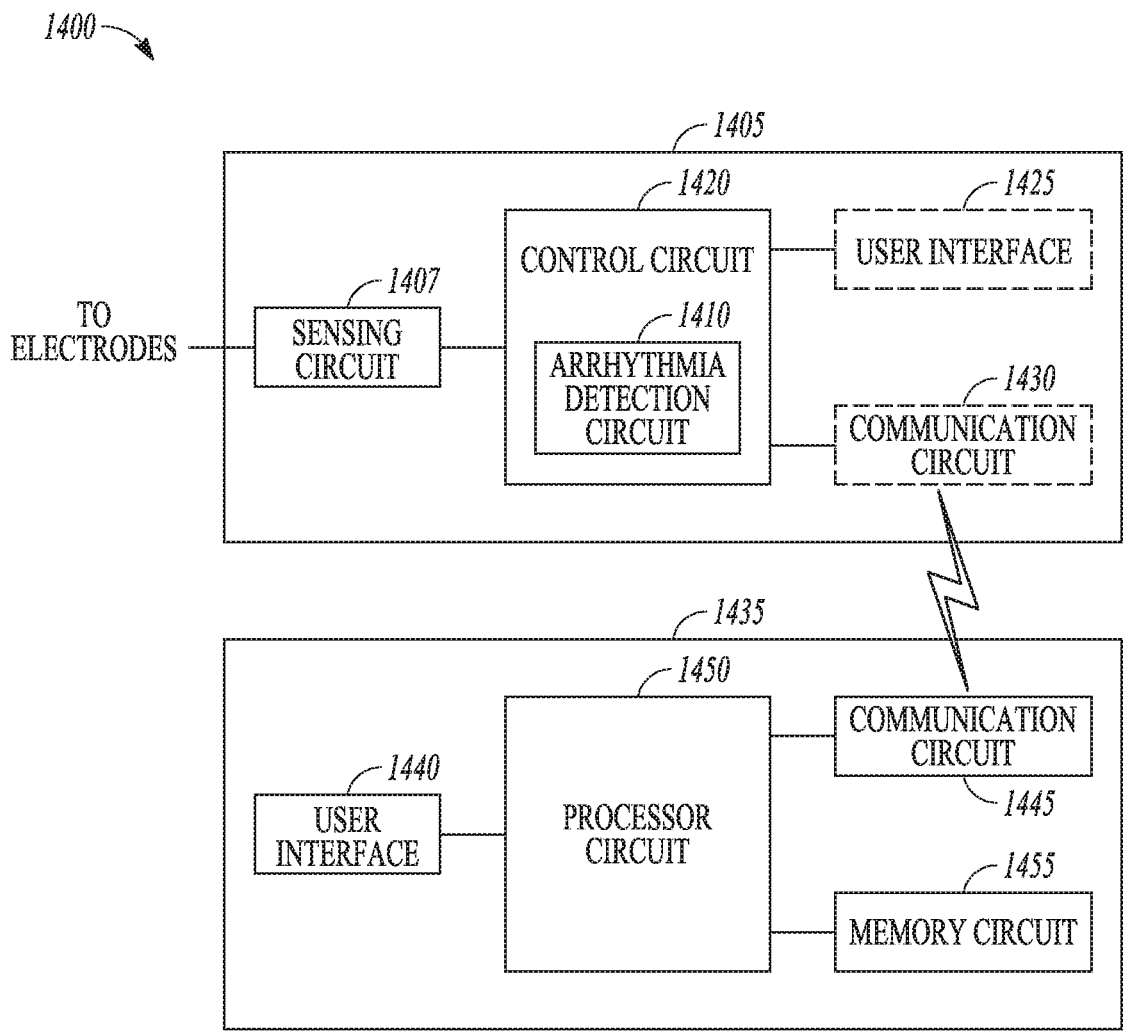
FIG. 14 shows a block diagram of portions of another example of a medical device system.

FIG. 14 shows a block diagram of portions of an example of a medical device system 1400. The system includes an ambulatory medical device 1405. The ambulatory medical device 1405 includes a sensing circuit 1407 that generates a sensed physiological signal representative of cardiac activity of a subject, and a control circuit 1420. The control circuit 1420 can include can include a microprocessor, a digital signal processor, application specific integrated circuit (ASIC), or other type of processor, interpreting or executing instructions included in software or firmware. The control circuit 1420 can include other circuits to perform the functions described. These circuits may include software, hardware, firmware or any combination thereof. Multiple functions can be performed in one or more of the circuits as desired.

The control circuit 1420 includes an arrhythmia detection circuit 1410 or sub-circuit that monitors V-V intervals using the physiological signal sensed by the sensing circuit 1407. The arrhythmia detection circuit 1410 determines a heart rate mode and an HRDI using the V-V intervals. The arrhythmia detection circuit 1410 determines differences between the monitored V-V intervals, and determines a measure of V-V interval dispersion using the determined V-V interval differences.

The arrhythmia detection circuit 1410 compares the determined heart rate mode to a specified heart rate mode threshold value, compares the determined HRDI to a specified HRDI threshold value, and compares the determined measure of V-V interval dispersion to a specified dispersion threshold value. The arrhythmia detection circuit 1410 generates an indication of AF when both of i) the determined measure of V-V interval dispersion satisfies the specified dispersion threshold value, and ii) the determined heart rate mode satisfies the specified heart rate mode threshold value or the determined HRDI satisfies the specified HRDI threshold value.

In some examples, the ambulatory medical device 1405 is a wearable medical device or a handheld medical device and includes a user interface 1425 that receives one or more of the specified dispersion threshold value, the specified heart rate mode threshold value, and the specified HRDI threshold value. The user interface 1425 may include one or more of a display, a mouse, a keyboard, and a touch sensitive or multi-touch sensitive display screen. The threshold values received through the user interface can be used to tune the AF detection by the ambulatory medical device 1405.

In some examples, the ambulatory medical device 1405 includes a communication circuit 1430 that communicates information wirelessly with a separate device. The system 1400 can include a second device 1435. The second device 1435 includes a user interface 1440 to receive values for one or more of the specified dispersion threshold value, the specified heart rate mode threshold value, and the specified HRDI threshold value. The second device 1435 also includes a communication circuit 1445 that communicates the one or more values wirelessly to the ambulatory medical device 1405. The second device 1435 allows a user to tune the threshold values for an implantable as well as for a wearable or a handheld medical device.

The user interface 1440 may present information to assist the user in setting threshold for one or both of the heart rate mode and the HRDI. In certain variations, the user interface 1440 presents suggested values for the heart rate mode and the HRDI thresholds. In certain variations, the user interface 1440 presents a graph to the user such as the graph shown in FIGS. 6 and 7 to present a distribution useful to the user in selecting thresholds for a heart rate mode or an HRDI.

In some examples, the threshold values of the detection methods are automatically tuned by the system 1400. The second device 1435 may include a processor circuit 1450. The processor circuit 1450 can include a microprocessor, a digital signal processor (DSP), application specific integrated circuit (ASIC), or other type of processor, interpreting or executing instructions included in software or firmware. The second device 1435 may also include a memory circuit 1455 integral to the processor circuit 1450 or in electrical communication with the processor circuit 1450.

The memory circuit 1455 may store information associated with one or more recorded arrhythmia episodes. The episodes may be sensed by the ambulatory medical device 1401 and communicated to the second device 1435. The processor circuit 1450 determines AF using the stored information and adjusts the value of one or more of the specified dispersion threshold value, the specified heart rate mode threshold value, and the specified HRDI threshold value according to the determination of AF. In certain examples, arrhythmia episodes are presented via the user interface and a user enters an assessment or judgment of whether the episodes represent AF. The processor circuit 1450 then adjusts the value of one or more of the specified dispersion threshold value, the specified heart rate mode threshold value, and the specified HRDI threshold value according to the indication of AF received via the user interface.

In certain embodiments, the processor circuit 1450 performs a learning algorithm to determine adjustments to the threshold values. This can include determining a performance measure of the AF detection by the ambulatory medical device 1401. The performance measure can include sensitivity, specificity, positive predictive value, or negative predictive value, among other things. Sensitivity refers to the ability of the detection scheme of a device to effectively detect AF or to distinguish AF from noise. Specificity refers to the ability of the detection scheme misidentifying rhythms that are not AF as AF. If the performance measure does not meet a specified performance criterion, the processor circuit 1450 can adjust or tune one or more of the threshold values. Thus, the processor circuit can tune individual detection methods separately.

In practice, optimizing an AF detection scheme may involve settling for a trade-off among performance measures, such as between sensitivity and specificity for instance. The ability to separately tune one detection method for sensitivity (e.g., easier to satisfy thresholds) and tune a second detection method for specificity (e.g., harder to satisfy thresholds) may improve the overall performance of combined AF detection methods.

ADDITIONAL NOTES AND EXAMPLES

Example 1 can include subject matter (such as an apparatus) comprising a sensing circuit configured to generate a sensed physiological signal representative of cardiac activity of a subject; and an arrhythmia detection circuit. The arrhythmia detection circuit is configured to monitor information corresponding to ventricular depolarization (V-V) intervals using the sensed physiological signal, determine a V-V interval distribution of V-V interval samples; determine a heart rate density index (HRDI) as a portion of samples of the V-V interval distribution corresponding to a V-V interval occurring most often in the distribution; and generate an indication of atrial fibrillation (AF) using the HRDI.

In Example 2, the subject matter of Example 1 optionally includes an arrhythmia detection circuit configured to determine a heart rate mode as a heart rate corresponding to a V-V interval value having most samples in the V-V interval distribution; determine the HRDI as the portion of the V-V intervals having the heart rate mode; and generate an indication of AF using the heart rate mode and the HRDI.

In Example 3 the subject matter of one or both of Example 1 and Example 2 optionally includes an arrhythmia detection circuit is configured to compare the heart rate mode to a specified heart rate mode threshold value; compare the HRDI to a specified HRDI threshold value; and generate the indication of AF when the determined heart rate mode satisfies the specified heart rate mode threshold value or the determined HRDI satisfies the threshold value.

In Example 4, the subject matter of one or any combination of Examples 1-3 optionally includes an arrhythmia detection circuit configured to determine differences between the monitored V-V intervals; determine a measure of V-V interval dispersion using the determined V-V interval differences; compare the measure of V-V interval dispersion to a specified dispersion threshold value; and generate the indication of AF when both of i) the determined measure of V-V dispersion satisfies the specified dispersion threshold value, and ii) the determined heart rate mode satisfies the specified heart rate mode threshold value or the determined HRDI satisfies the specified HRDI threshold value.

In Example 5, the subject matter of Example 4 optionally includes a measure of V-V interval dispersion including a variance of the determined interval differences; and wherein the arrhythmia detection circuit is configured to generate the indication of AF when both of i) the determined variance satisfies a specified variance threshold value and ii) the determined heart rate mode satisfies the specified heart rate mode threshold value or the determined HRDI satisfies the specified HRDI threshold value.

In Example 6, the subject matter of one or both of Example 4 or Example 5 optionally includes a measure of V-V interval dispersion including a first ratio determined using a number of stable interval differences and a number of unstable interval differences, and a second ratio determined using a number of unstable-random interval differences and a sum including the number of stable interval differences and the number of unstable interval differences; and wherein the arrhythmia detection circuit is configured to generate the indication of AF when both of i) the first ratio satisfies a specified first ratio threshold value and the determined second ratio satisfies a specified second ratio threshold value, and ii) the determined heart rate mode satisfies the specified heart rate mode threshold value or the determined. HRDI satisfies the specified HRDI threshold value.

In Example 7, the subject matter of Example 6 optionally includes an arrhythmia detection circuit configured to classify an interval difference as stable when the interval difference is less than a specified threshold difference value from an immediately previous interval difference; classify the interval difference as unstable when the interval difference is more than the specified threshold difference value from the immediately previous interval difference; and classify the interval difference as unstable-random when the magnitude of the interval difference is more than the specified threshold difference value from the immediately previous interval difference and the interval difference is a negative value that satisfies a specified negative value threshold.

In Example 8, the subject matter of one or both of Examples 5 and Example 6 optionally includes one or more of the specified first ratio threshold value, the specified second ratio threshold value, the specified heart rate mode threshold value, and the specified HRDI threshold value being adjustable to cause the specified first ratio threshold value and the specified second ratio threshold value to be more sensitive to detection of AF than the specified heart rate mode threshold value and the specified HRDI threshold value, or to cause the specified heart rate mode threshold value and the specified HRDI threshold value to be more sensitive to detection of AF than the specified first ratio threshold value and the specified second ratio threshold value.

In Example 9, the subject matter of one or any combination of Examples 4-8 optionally includes an arrhythmia detection circuit configured to determine measure of V-V interval dispersion over a duration of time different from a duration of time used to determine the heart rate mode and HRDI.

In Example 10, the subject matter of one or any combination of Examples 1-9 optionally includes a therapy circuit configured for coupling to electrodes to provide an anti-arrhythmic cardiac therapy to a subject, and a control circuit configured to initiate delivery of an anti-arrhythmic therapy in response to the generated indication.

In Example 11, the subject matter of one or any combination of Examples 1-10 optionally includes a sensing circuit configured to be coupled to an implantable electrode included in a lead arranged for placement of the implantable in a heart chamber.

In Example 12, the subject matter of one or any combination of Examples 1-11 optionally includes a sensing circuit configured to be coupled to an implantable electrode included in a leadless implantable medical device.

In Example 13, the subject matter of one or any combination of Examples 1-12 optionally includes a sensing circuit configured to be coupled to a subcutaneously implantable electrode that is configured to sense cardiac signals without direct cardiac contact with the subject.

In Example 14, the subject matter of one or any combination of Examples 1-13 optionally includes a sensing circuit and an arrhythmia detection circuit included in a wearable device or a handheld device.

Example 15 can include subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-14 to include such subject matter, comprising monitoring information corresponding to ventricular depolarization (V-V) intervals of a subject; determining a V-V interval distribution using sampled V-V interval values; determining a heart rate density index (HRDI) as a portion of the sampled. V-V interval values corresponding to a V-V interval occurring most often in the distribution; comparing the HRDI to a specified HRDI threshold value; and generating an indication of AF when the determined HRDI satisfies the HRDI threshold value.

In Example 16 the subject matter of Example 15 can optionally include determining a heart rate mode as the heart rate corresponding to a V-V interval value having most samples in the V-V interval distribution; determining the HRDI as the portion of the V-V intervals having the heart rate mode; comparing the heart rate mode to a specified heart rate mode threshold value; and generating the indication of AF when the determined heart rate mode satisfies the specified heart rate mode threshold value or the determined HRDI satisfies the HRDI threshold value.

Example 17 can include subject matter (such as a system including an ambulatory medical device), or can optionally be combined with the subject matter of one or any combination of Examples 1-16 to include such subject matter, comprising an ambulatory medical device that including a sensing circuit configured to generate a sensed physiological signal representative of cardiac activity of a subject; and a control circuit. The control circuit optionally includes an arrhythmia detection circuit configured to monitor ventricular depolarization (V-V) intervals using the sensed physiological signal; determine a heart rate mode using the V-V intervals; determine a heart, rate density index (HRDI) using the V-V intervals, wherein the HRDI is a portion of the V-V intervals having the heart rate mode; determine differences between the monitored V-V intervals; determine a measure of V-V interval dispersion using the determined V-V interval differences; compare the determined heart rate mode to a specified heart rate mode threshold value and compare the determined HRDI to a specified HRDI threshold value; compare the determined measure of V-V interval dispersion to a specified dispersion threshold value; and generate an indication of AF when both of i) the determined measure of V-V interval dispersion satisfies the specified dispersion threshold value, and ii) the determined heart rate mode satisfies the specified heart rate mode threshold value or the determined HRDI satisfies the specified HRDI threshold value.

In Example 18, the subject matter of Example 17 optionally includes a second device and an ambulatory medical device including a communication circuit configured to communicate information with the second device. The second device includes a communication circuit configured for communication with the ambulatory medical device, a memory circuit configured to store information associated with recorded arrhythmia episodes, and a processor circuit configured to determine AF using the stored information and adjust the value of one or more of the specified dispersion threshold value, the specified heart rate mode threshold value, and the specified HRDI threshold value according to the determination of AF.

In Example 19, the subject matter of Example 17 optionally includes a second device and an ambulatory medical device including a communication circuit configured to communicate information with the second device. The second device includes a user interface configured to receive values for one or more of the specified dispersion threshold value, the specified heart rate mode threshold value, and the specified HRDI threshold value; and a communication circuit configured to communicate the one or more values to the ambulatory medical device.

In Example 20, the subject matter of claim 17 optionally includes an ambulatory medical device including a user interface configured to receive one or more of the specified dispersion threshold value, the specified heart rate mode threshold value, and the specified HRDI threshold value.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   an arrhythmia detection circuit configured to:
   receive a physiological signal representative of cardiac activity of one or both ventricles of the subject;
   determine ventricular depolarization (V-V) intervals of a subject using the physiological signal;
   determine a heart rate density index (HRDI) using the V-V intervals; and
   determine an indication of atrial fibrillation (AF) using the determined HRDI.

2. The system of claim 1, wherein the arrhythmia detection circuit is configured to:
   determine a V-V interval distribution using the determined V-V intervals; and
   determine the HRDI corresponding to a V-V interval occurring most often in the determined V-V interval distribution.

3. The system of claim 1, wherein the arrhythmia detection circuit is configured to:
   determine a heart rate mode using the V-V intervals; and
   determine the HRDI as a fraction of the V-V intervals corresponding to the heart rate mode.

4. The system of claim 1, wherein the arrhythmia detection circuit is configured to:
   determine a heart rate distribution using the V-V interval samples; and
   determine the HRDI as a measure of one or both of a skew and a kurtosis of the heart rate distribution.

5. The system of claim 1, wherein the arrhythmia detection circuit is configured to compare the determined HRDI to an AF detection HRDI threshold; and
   determine the indication of AF when the determined HRDI satisfies the AF detection HRDI threshold.

6. The system of claim 1, wherein the arrhythmia detection circuit is configured to:
   determine a heart rate mode using the V-V intervals;
   compare the heart rate mode to a specified heart rate mode threshold value;
   compare the HRDI to a specified HRDI threshold value; and
   determine the indication of AF when one or both of the determined heart rate mode satisfies the specified heart rate mode threshold value and the determined HRDI satisfies the HRDI threshold value.

7. The system of claim 1, wherein the arrhythmia detection circuit is configured to:
   determine a heart rate mode using the V-V intervals;
   determine differences between the monitored V-V intervals;
   determine a measure of V-V interval dispersion using the determined V-V interval differences;
   compare the measure of V-V interval dispersion to a specified dispersion threshold value; and
   determine the indication of AF when both of i) the determined measure of V-V dispersion satisfies the specified dispersion threshold value, and ii) the determined heart rate mode satisfies the specified heart rate mode threshold value or the determined HRDI satisfies the specified HRDI threshold value.

8. The system of claim 7, wherein the measure of V-V interval dispersion includes a variance of the determined interval differences; and
wherein the arrhythmia detection circuit is configured to determine the indication of AF when both of i) the determined variance satisfies a specified variance threshold value and ii) the determined heart rate mode satisfies the specified heart rate mode threshold value or the determined HRDI satisfies the specified HRDI threshold value.

9. The system of claim 7, wherein the measure of V-V interval dispersion includes a first ratio determined using a number of stable interval differences and a number of unstable interval differences, and a second ratio determined using a number of unstable-random interval differences and a sum including the number of stable interval differences and the number of unstable interval differences; and
wherein the arrhythmia detection circuit is configured to determine the indication of AF when both of i) the first ratio satisfies a specified first ratio threshold value and the determined second ratio satisfies a specified second ratio threshold value, and ii) the determined heart rate mode satisfies the specified heart rate mode threshold value or the determined HRDI satisfies the specified HRDI threshold value.

10. The system of claim 1, including a sensing circuit operatively coupled to the arrhythmia detection circuit and configured to sense the physiological signal representative of cardiac activity of one or both ventricles when coupled to one or more sensing electrodes configured for arrangement at the one or both ventricles of the subject.

11. The system of claim 1, including a therapy circuit configured for coupling to electrodes to provide an anti-arrhythmic cardiac therapy to a subject, and a control circuit operatively coupled to the arrhythmia detection circuit and the therapy circuit, and configured to initiate delivery of an anti-arrhythmic therapy according to the determined indication of AF.

12. The system of claim 1, including the one or more sensing electrodes operatively coupled to the sensing circuit, wherein the one or more sensing electrodes include at least one implantable electrode included in a lead arranged for placement of the implantable electrode in a heart chamber.

13. The system of claim 1, including the one or more sensing electrodes operatively coupled to the sensing circuit, wherein the one or more sensing electrodes are included in a leadless implantable medical device.

14. The system of claim 1, including the one or more sensing electrodes operatively coupled to the sensing circuit, wherein the one or more sensing electrodes include at least one subcutaneously implantable electrode configured to sense cardiac signals without direct cardiac contact with the subject.

15. A method of operating an ambulatory medical device, the method comprising:
determining ventricular depolarization (V-V) intervals of a subject using a sensed physiological signal representative of cardiac activity of one or both ventricles of the subject;
determining a heart rate mode using the determined V-V intervals;
determining a heart rate density index (HRDI) using the determined V-V intervals;
comparing the heart rate mode and the HRDI to specified thresholds; and
producing an indication of atrial fibrillation (AF) using the determined HRDI and the determined heart rate mode.

16. The method of claim 15, including determining a V-V interval distribution using the determined V-V intervals, wherein determining the HRDI includes determining the HRDI corresponding to a V-V interval occurring most often in the determined V-V interval distribution.

17. The method of claim 15, wherein determining the HRDI includes determining the HRDI as a fraction of the V-V intervals corresponding to the heart rate mode.

18. The method of claim 15, including determining a heart rate distribution using the V-V interval samples, wherein determining the HRDI includes determining the HRDI as a measure of one or both of a skew and a kurtosis of the heart rate distribution.

19. The method of claim 15, including comparing the determined HRDI to an AF detection HRDI threshold, wherein determining the indication of AF includes when the determined HRDI satisfies the AF detection HRDI threshold.

20. The method of claim 15, including generating the physiologic signal representative of cardiac activity at one or both ventricles of the subject using electrodes operatively coupled to the ambulatory medical device.

* * * * *